United States Patent
Mako, Jr. et al.

(10) Patent No.: US 10,094,498 B2
(45) Date of Patent: Oct. 9, 2018

(54) METHOD FOR JOINING CERAMICS TO CERAMICS OR CERAMICS TO METALS, AND APPARATUS

(71) Applicants: Frederick M. Mako, Jr., Fairfax Station, VA (US); Edward Jeffrey Cruz, Sterling, VA (US); Frederick M. Mako, Fairfax Station, VA (US)

(72) Inventors: Frederick M. Mako, Jr., Fairfax Station, VA (US); Edward Jeffrey Cruz, Sterling, VA (US); Frederick M. Mako, Fairfax Station, VA (US)

(73) Assignee: Frederick M. Mako, Jr., Fairfax Station, VA (US)

( * ) Notice: Subject to any disclaimer, the term of this patent is extended or adjusted under 35 U.S.C. 154(b) by 609 days.

(21) Appl. No.: 14/671,283

(22) Filed: Mar. 27, 2015

(65) Prior Publication Data

US 2015/0260322 A1 Sep. 17, 2015

Related U.S. Application Data

(63) Continuation-in-part of application No. 14/646,253, filed on Mar. 12, 2015.

(Continued)

(51) Int. Cl.
*C04B 37/00* (2006.01)
*F16L 25/00* (2006.01)
(Continued)

(52) U.S. Cl.
CPC ........ *F16L 25/0081* (2013.01); *B23K 35/302* (2013.01); *B23K 35/304* (2013.01); *B23K 35/327* (2013.01); *B32B 1/08* (2013.01); *B32B 7/12* (2013.01); *B32B 9/005* (2013.01); *B32B 9/041* (2013.01); *B32B 15/043* (2013.01); *C04B 37/005* (2013.01); *C04B 37/025* (2013.01); *F16J 15/0806* (2013.01); *F16L 13/0209* (2013.01); *F16L 21/002* (2013.01); *F16L 25/0072* (2013.01); *F16L 49/02* (2013.01);

(Continued)

(58) Field of Classification Search
CPC ................ C04B 37/005; C04B 35/565; C04B 2237/765; C04B 2235/96; C04B 2237/84; C04B 37/003; C04B 37/006; C04B 37/02

See application file for complete search history.

(56) References Cited

U.S. PATENT DOCUMENTS 3,265,473 A * 8/1966 Gallet ................... C04B 37/006
428/632
3,457,052 A * 7/1969 Carlson ................. C04B 37/006
428/633

(Continued)

*Primary Examiner* — David Bochna
(74) *Attorney, Agent, or Firm* — Ansel M. Schwartz

(57) ABSTRACT

An assembly including a ceramic body. The assembly comprises a tungsten coupling attached to the ceramic body with a first joint that forms a first helium tight seal between the ceramic body and the tungsten coupling and where the first helium tight seal maintains its integrity at a temperature over 400° C. The assembly includes a metal body attached to the tungsten coupling with a second joint that forms a second helium tight seal between the metal body and the tungsten coupling and where the second helium tight seal maintains its integrity at a temperature over 400° C. A method. A mixture. A coupling.

6 Claims, 14 Drawing Sheets

Related U.S. Application Data

(60) Provisional application No. 61/952,492, filed on Mar. 13, 2014, provisional application No. 61/971,941, filed on Mar. 28, 2014, provisional application No. 61/972,582, filed on Mar. 31, 2014, provisional application No. 61/972,630, filed on Mar. 31, 2014, provisional application No. 61/973,027, filed on Mar. 31, 2014, provisional application No. 61/973,085, filed on Mar. 31, 2014.

(51) Int. Cl.

| | | |
|---|---|---|
| *B23K 35/32* | (2006.01) | |
| *B32B 7/12* | (2006.01) | |
| *B32B 15/04* | (2006.01) | |
| *B32B 9/00* | (2006.01) | |
| *B32B 9/04* | (2006.01) | |
| *B32B 1/08* | (2006.01) | |
| *B23K 35/30* | (2006.01) | |
| *F16L 13/02* | (2006.01) | |
| *F16L 21/00* | (2006.01) | |
| *F16L 49/02* | (2006.01) | |
| *F16J 15/08* | (2006.01) | |
| *C04B 37/02* | (2006.01) | |

(52) U.S. Cl.
CPC ....... *B32B 2255/06* (2013.01); *B32B 2255/20* (2013.01); *B32B 2255/205* (2013.01); *B32B 2307/7242* (2013.01); *B32B 2597/00* (2013.01); *C04B 2235/5436* (2013.01); *C04B 2235/6562* (2013.01); *C04B 2237/062* (2013.01); *C04B 2237/341* (2013.01); *C04B 2237/365* (2013.01); *C04B 2237/403* (2013.01); *C04B 2237/405* (2013.01); *C04B 2237/708* (2013.01); *C04B 2237/765* (2013.01); *C04B 2237/84* (2013.01); *Y10T 428/12292* (2015.01); *Y10T 428/12549* (2015.01); *Y10T 428/13* (2015.01); *Y10T 428/1317* (2015.01)

(56) References Cited

U.S. PATENT DOCUMENTS

| | | | | |
|---|---|---|---|---|
| 3,549,337 | A * | 12/1970 | Palmer | C04B 37/006 228/121 |
| 3,589,881 | A * | 6/1971 | Langley et al. | C04B 37/006 220/2.1 A |
| 3,878,425 | A * | 4/1975 | Katz | C04B 37/006 228/120 |
| 4,729,504 | A * | 3/1988 | Edamura | C04B 37/006 228/122.1 |
| 5,013,612 | A * | 5/1991 | Hunt | C04B 37/006 428/469 |
| 2006/0019044 | A1* | 1/2006 | Watanabe | C04B 37/006 428/34.4 |
| 2010/0327537 | A1* | 12/2010 | Johnson | C04B 37/006 277/405 |
| 2011/0024431 | A1* | 2/2011 | Yano | F16J 12/00 220/581 |
| 2011/0297269 | A1* | 12/2011 | Pilon | F16L 9/02 138/141 |

\* cited by examiner

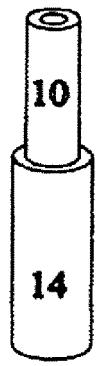
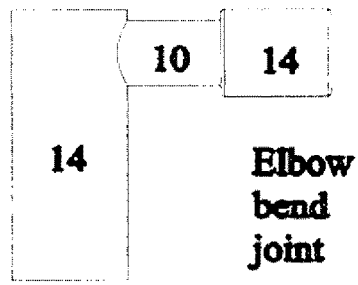
Large diameter to small diameter lap joint
Elbow bend joint
FIG. 3a    FIG. 3b
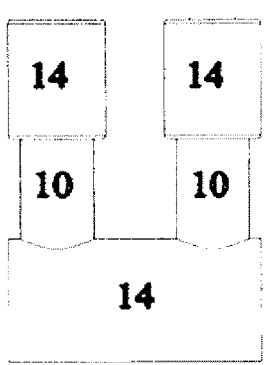
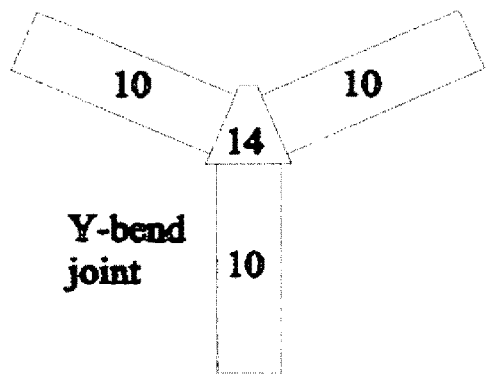
U-bend joint
Y-bend joint
FIG. 3c    FIG. 3d

_US 10,094,498 B2_

METHOD FOR JOINING CERAMICS TO CERAMICS OR CERAMICS TO METALS, AND APPARATUS

CROSS-REFERENCE TO RELATED APPLICATIONS

This is a continuation-in-part of U.S. patent application Ser. No. 14/656,253 filed Mar. 12, 2015, and is a nonprovisional of U.S. provisional applications Ser. No. 61/971,941 filed Mar. 28, 2014; 61/972,582 filed Mar. 31, 2014; 61/972,630 filed Mar. 31, 2014; 61/973,027 filed Mar. 31, 2014; and 61/973,085 filed Mar. 31, 2014, all of which are incorporated by reference herein.

FIELD OF THE INVENTION

The present invention is related to an assembly formed of ceramic bodies and/or ceramic bodies and metal bodies with a tungsten coupling. (As used herein, references to the "present invention" or "invention" relate to exemplary embodiments and not necessarily to every embodiment encompassed by the appended claims.) More specifically, the present invention is related to an assembly formed of ceramic bodies and/or ceramic bodies and metal bodies with a tungsten coupling where the ceramic bodies are made of either Silicon Carbide or Mullite, and the metal bodies are made of superalloy or steal.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

High temperature (800° C. to 1450° C.) engineering materials, such as Silicon Carbide (SiC), Tungsten (W), Molybdenum (Mo) or Osmium (Os), have many desirable properties, but are often difficult to manufacture in large sizes or complex geometries. These materials are also very difficult to join and hermetically seal to with existing technologies in such a way that they are still suitable for desired high temperature applications. The ability to employ materials that can withstand higher temperature than what the current state of the art offers can often have tremendous benefits, examples of which include increased production volume from ethylene plants or increased safety margins for nuclear reactors. The present invention allows extended application of SiC by allowing for it to be joined to metals such that the joining material does not negatively affect the high temperature performance of the bulk materials, including, but not limited to, when the joining material is present in the high temperature environment.

High temperature engineering materials, such as Tungsten (W), have many desirable properties, but are often limited to use in vacuum or inert atmosphere environments. The ability to employ materials, specifically W, which can withstand higher temperature than what the current state of the art offers, can often have tremendous benefits. This could, for example, result in increased production volume from ethylene plants. The present invention allows extended application of W by allowing for it to be joined to Inconel 600 for use at elevated temperature (up to 1150° C.) without negatively affecting the high temperature performance of the bulk materials.

BRIEF SUMMARY OF THE INVENTION

The subject invention relates to a method for joining bodies of ceramic and/or metals, specifically: silicon carbide, mullite or tungsten to silicon carbide, mullite or tungsten and tungsten to stainless steel or superalloys. Joints are produced using joining materials developed by FM Technologies, Inc. The joints are enhanced by the inclusion of alignment geometry in the bodies to be joined. The joints are enhanced by the constraint of the joining material to the joint region by a capture geometry of the ceramic or metal bodies.

The present invention pertains to an assembly. The assembly comprises a ceramic body. The assembly comprises a tungsten coupling attached to the ceramic body with a first joint that forms a first helium tight seal between the ceramic body and the tungsten coupling and where the first helium tight seal maintains its integrity at a temperature over 1100° C. The assembly comprises a metal body attached to the tungsten coupling with a second joint that forms a second helium tight seal between the metal body and the tungsten coupling and where the second helium tight seal maintains its integrity at a temperature over 1000° C.

The present invention pertains to a method of forming an assembly. The method comprises the steps of forming a first joint between a ceramic body and a tungsten coupling to create a healing first helium tight seal between the tungsten coupling and the ceramic body where the first helium tight seal maintains its integrity at a temperature over 1100° C. There is the step of forming a second joint between the tungsten coupling and a metal body to create a second helium tight seal between the tungsten coupling and the metal body where the second helium tight seal maintains its integrity at a temperature over 1100° C.

The present invention pertains to an assembly. The assembly comprises a first ceramic body. The assembly comprises a second ceramic body attached to the first ceramic body with a first joint that forms a first helium tight seal between the first ceramic body and the second ceramic body and where the first helium tight seal maintains its integrity at a temperature over 1100° C.

The present invention pertains to a method of forming an assembly. The method comprises the steps of placing a first ceramic body adjacent a second ceramic body. There is the step of forming a first joint between the first ceramic body and the second ceramic body to create a first helium tight seal between the first and second ceramic bodies where the first helium tight seal maintains its integrity at a temperature over 1100° C.

The present invention pertains to a coupling. The coupling comprises a member made of tungsten having an outer surface. The coupling has a coating disposed on the outer surface in its entirety so no portion of any surface of the member is exposed. The coating is made of an oxidation resistant material so the member 30 maintains its integrity above 400° C. and does not oxidize. The member may be hollow having an inner surface 36 about the hollow. The coating is disposed on the inner and outer surfaces in their entirety so no portion of any surface of the member is exposed; the coating made of an oxidation resistant material so the member maintains its integrity above 400 degrees C. and has an effective protective oxidization coating above 400° C.

The present invention pertains to a method for making a coupling. The method comprises the steps of placing a coating on all surfaces of a tungsten member with an oxidation resistant material so the member maintains its integrity above 400 degrees C. and has an effective protective oxidization coating above 400° C. There is the step of letting the coating dry.

The present invention pertains to a method of joining silicon carbide to silicon carbide by using a mixed oxide material consisting essentially of alumina (Al2O3), silica (SiO2) and magnesia (MgO), with additions of less than 4 wt % of TiO2, Fe2O3, CaO, NaO2, K2O, P2O5 and a sintering aid. The method comprises the steps of applying the mixed oxide material on a joining portion of the silicon carbide to silicon carbide. There is the step of heating the applied mixed oxide material to a temperature between 1550° C. and 1800° C. to form a semi-liquidus or a liquidus phase and holding for a time of order of minutes, thereby forming a brazing joint. There is the step of cooling the heated mixed oxide material to form a "braze-like" joint.

BRIEF DESCRIPTION OF THE SEVERAL VIEWS OF THE DRAWING

In the accompanying drawings, the preferred embodiment of the invention and preferred methods of practicing the invention are illustrated in which:

FIG. 3a is a perspective view of a large diameter to small diameter lap joint.

FIG. 3b is a perspective view of an elbow bend joint.

FIG. 3c is a perspective view of U bend joint.

FIG. 3d is a perspective view of a Y bend joint.

DETAILED DESCRIPTION OF THE INVENTION

Figure 11:
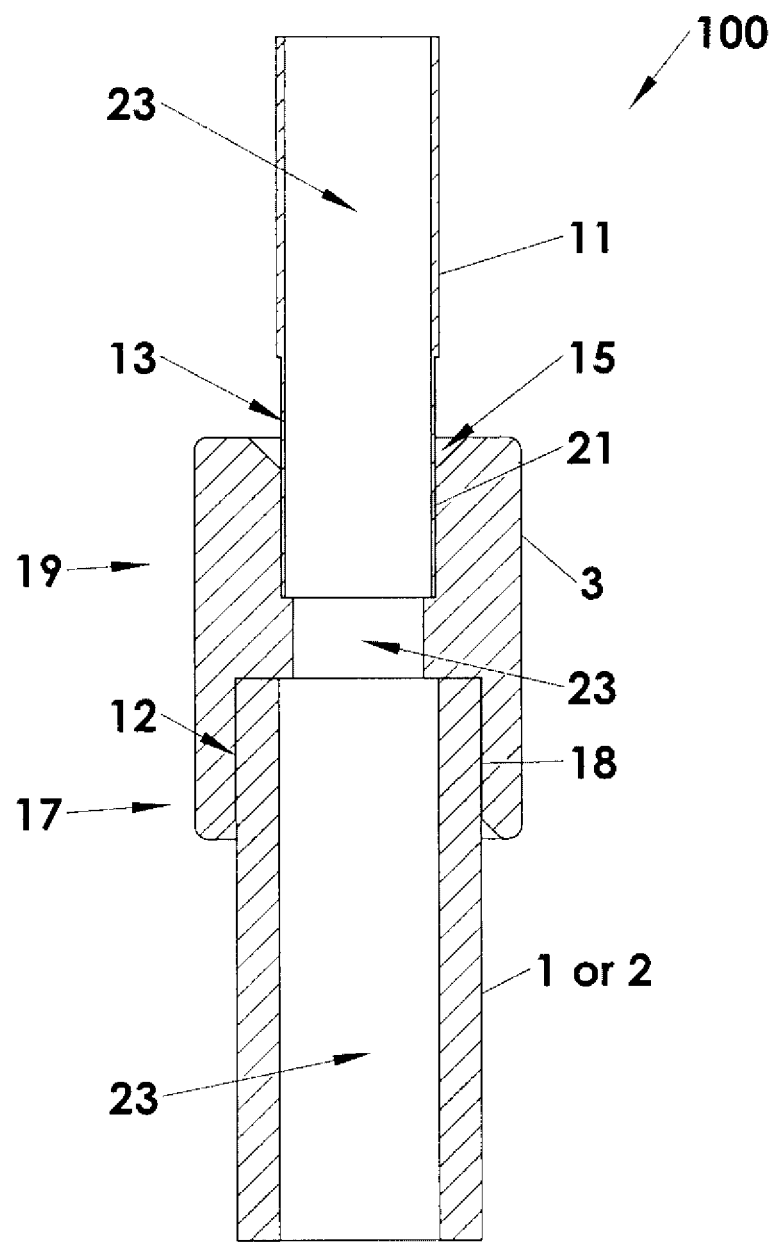
FIG. 11 is a representation of a ceramic to metal joint with tungsten coupling.

Referring now to the drawings wherein like reference numerals refer to similar or identical parts throughout the several views, and more specifically to FIG. 11 thereof, there is shown an assembly 100. The assembly 100 comprises a ceramic body 1 or 2. The assembly 100 comprises a tungsten coupling 3 attached to the ceramic body 1 or 2 with a first joint 17 that forms a first helium tight seal 18 between the ceramic body 1 or 2 and the tungsten coupling 3 and where the first helium tight seal 18 maintains its integrity at a temperature over 400° C. and even 500° C. or 600° C. or 700° C. or 1000° C. The assembly 100 comprises a metal body 11 attached to the tungsten coupling 3 with a second joint 19 that forms a second helium tight seal 21 between the metal body 11 and the tungsten coupling 3 and where the second helium tight seal 21 maintains its integrity at a temperature over 400° C. and even 500° C. or 600° C. or 700° C. or 1000° C.

The ceramic body 1 or 2, the tungsten coupling 3 and the metal body 11 may be hollow and form a continuous channel 23 extending through and inside the ceramic body 1 or 2, the tungsten coupling 3, the metal body 11 and the first and second helium tight seals. The ceramic body 1 or 2 may be made of silicon carbide and the metal body 11 may be made of super alloy. The first joint 17 may be made of between 30 wt % (weight percent or percent by mass) and 80 wt %, nominally 60 wt %, alumina-silicate, also known as Lava or Wonder Stone, and between 20 wt % and 70 wt %, nominally 40 wt %, magnesia-silicate, also known as Steatite. The alumina-silicate and magnesia-silicate are mixed in powder form to a 100% weight fraction to form Makotite™. Alternatively, the first joint 17 may be made of between 16.8 wt % and 35.8 wt %, nominally 28.2 wt %, alumina, between 57.9 wt % and 61.2 wt %, nominally 59.2 wt %, silica and between 6.3 wt % and 22.0 wt %, nominally 12.6 wt %, magnesia. The alumina, silica and magnesia are mixed in powder form to a 100% weight fraction to form Makotite™. The second joint 21 may be made of a mixture of 10 wt %-80 wt % 80/20 nickel-chromium alloy powder, also known as Nichrome V, and 20 wt %-90 wt % copper wire or grain of ≥99.99% purity. The best resultant alloy is nominally 33 wt % of 80/20 nickel-chromium alloy and 67 wt % copper.

The metal body 11 may be attached to the tungsten coupling 3 attached to the ceramic body 1 or 2 aligned to define a straight line. Alternatively, the metal body 11 may be attached to the tungsten coupling 3 attached to the ceramic body 1 or 2 to define a bend.

The present invention pertains to a method of forming an assembly 100. The method comprises the steps of forming a first joint 17 between a ceramic body 1 or 2 and a tungsten coupling 3 to create a first helium tight seal 18 between the tungsten coupling 3 and the ceramic body 1 or 2 where the first helium tight seal 18 maintains its integrity at a temperature over 400° C. There is the step of forming a second joint 19 between the tungsten coupling 3 and a metal body 11 to create a second helium tight seal 21 between the tungsten coupling 3 and the metal body 11 where the second helium tight seal 21 maintains its integrity at a temperature over 400° C.

Figure 1:
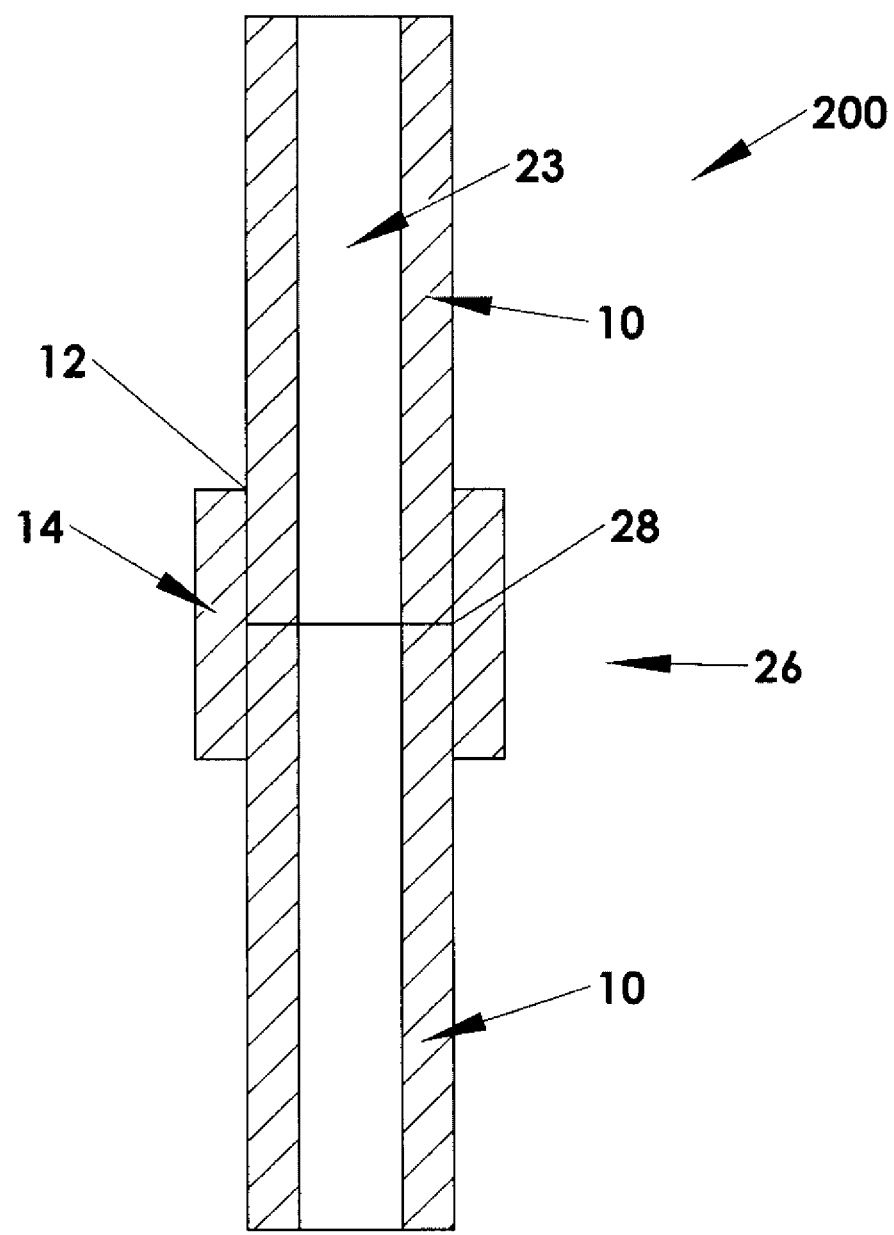
FIG. 1 is a cross-sectional view of a collar around ceramic bodies.

The present invention pertains to an assembly 200, as shown in FIG. 1. The assembly 200 comprises a first ceramic body 10. The assembly 200 comprises a second ceramic body 10 attached to the first ceramic body 10 with a first joint 26 that forms a first helium tight seal 28 between the first ceramic body 10 and the second ceramic body 10 and where the first helium tight seal 28 maintains its integrity at a temperature over 1100° C. or 1200° C. and even 1300° C. or 1400° C. or 1500° C.

The first ceramic body 10 and the second ceramic body 10 may be hollow and form a continuous channel 23 extending through and inside the first ceramic body 10 and the second ceramic body 10 and the first helium tight seal 28. The first ceramic body 10 may be made of silicon carbide and the second ceramic body 10 may be made of either silicon carbide or 3:2 mullite.

The first joint 26 may be made of between 30 wt % (weight percent or percent by mass) and 80 wt %, nominally 60 wt %, alumina-silicate, also known as Lava or Wonder Stone, and between 20 wt % and 70 wt %, nominally 40 wt %, magnesia-silicate, also known as Steatite. The alumina-silicate and magnesia-silicate are mixed in powder form to a 100% weight fraction to form Makotite™. Alternatively, the first joint may be made of between 16.8 wt % and 35.8 wt %, nominally 28.2 wt %, alumina, between 57.9 wt % and 61.2 wt %, nominally 59.2 wt %, silica and between 6.3 wt % and 22.0 wt %, nominally 12.6 wt %, magnesia. The alumina, silica and magnesia may be mixed in powder form to a 100% weight fraction to form Makotite™.

The first ceramic body 10 attached to the second ceramic body 10 may align to define a straight line. The first ceramic body 10 attached to the second ceramic body 10 may define a bend. The first ceramic body 10 may be attached to the second ceramic body 10 to define a manifold.

The present invention pertains to a method of forming an assembly 200. The method comprises the steps of placing a first ceramic body 19 adjacent a second ceramic body 10. There is the step of forming a first joint 26 between the first ceramic body 10 and the second ceramic body 10 to create a first helium tight seal 28 between the first and second ceramic bodies where the first helium tight seal 28 maintains its integrity at a temperature over 1100° C.

Figure 12:
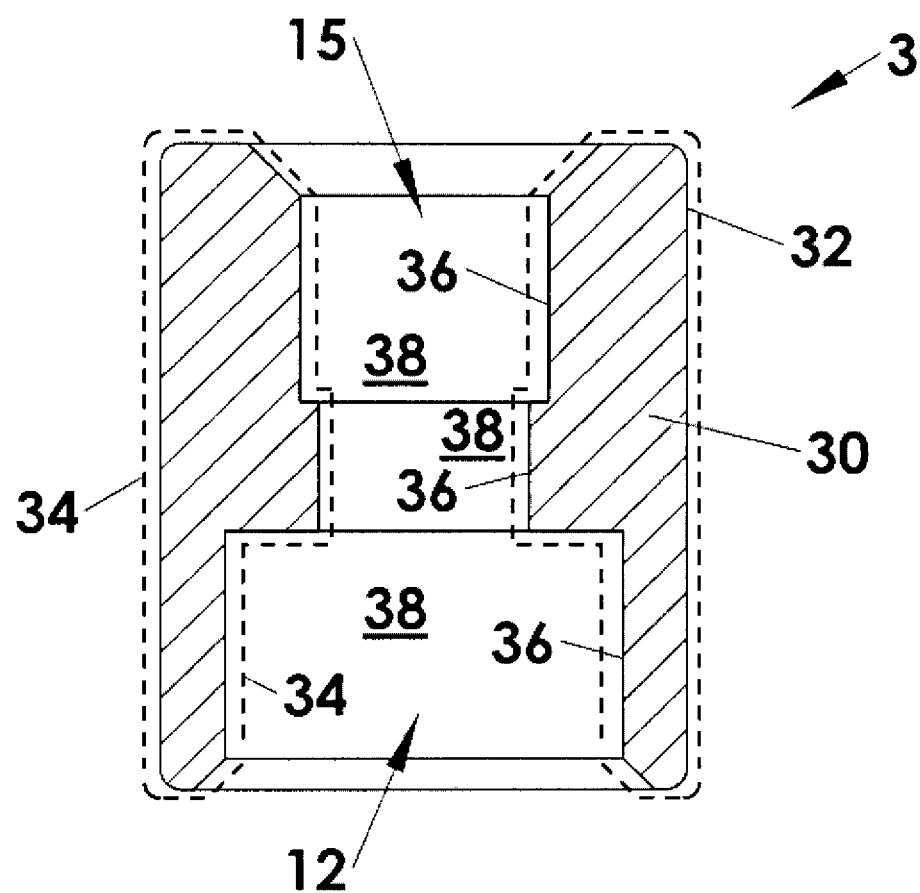
FIG. 12 is a representation of a tungsten coupling.

As shown in FIG. 12, the present invention pertains to a coupling 3. The coupling 3 comprises a member 30 made of tungsten having an outer surface 32. The coupling 3 has a coating 34 disposed on the outer surface 32 in its entirety so no portion of any surface of the member 30 is exposed. The coating 34 is made of an oxidation resistant material so the member 30 maintains its integrity above 400° C. (and even 500° C. or 600° C. or 800° C. or 1000° C.) and has an effective protective oxidization coating above 400° C. and even 500° C. or 600° C. or 800° C. or 1000° C. The member 30 may be hollow having an inner surface 36 about the hollow 38. The coating 34 is disposed on the inner and outer surfaces in their entirety so no portion of any surface of the member is exposed, the coating 34 made of an oxidation resistant material so the member maintains its integrity above 400° C. and does not oxidize.

The present invention pertains to a method for making a coupling 14. The method comprises the steps of placing a coating 34 on all surfaces of a tungsten member 30 with an oxidation resistant material so the member 30 maintains its integrity above 400° C. and has an effective protective oxidization coating above 400° C. There is the step of letting the coating dry.

The present invention pertains to a method of joining silicon carbide to silicon carbide by using a mixed oxide material consisting essentially of alumina (Al2O3), silica (SiO2) and magnesia (MgO), with additions of less than 4 wt % of TiO2, Fe2O3, CaO, NaO2, K2O, P2O5 and a sintering aid. The method comprises the steps of applying the mixed oxide material on a joining portion of the silicon carbide to silicon carbide. There is the step of heating the applied mixed oxide material to a temperature between 1550° C. and 1800° C. to form a semi-liquidus or a liquidus phase and holding for a time of order of minutes, thereby forming a brazing joint. There is the step of cooling the heated mixed oxide material to form a "braze-like" joint.

The mixed oxide material may have a form of powder or casting. The silicon carbide to silicon carbide may have a joint in a form of one of tube, plate and rod and any shape. The silicon carbide may be formed by sintering, chemical vapor deposition, or composite fiber matrix. The mixed oxide material may include Steatite and Mulcoa.

The joining portion may have a coefficient of thermal expansion between 1.5×10-6/K and 6×10-6/K. The brazed joint may form a hermetic joint between similar or dissimilar silicon carbide types, where the hermetic joints are defined by an ability to seal to such a degree that a passage of atoms or molecules with a size greater than or equal to that of a Helium atom cannot occur. The brazed joint may form a hermetic joint between dissimilar silicon carbide types with a coefficient of thermal expansion mismatch.

In the operation of the invention, the forms of ceramic and metal bodies 10 and 14, specifically: silicon carbide, (3:2) mullite or tungsten bodies 10 and 14 capable of being joined by the described method include shapes, such as, plate, rod, ball, tube, and others. These bodies 10 and 14 may be joined to either similar or dissimilar silicon carbide, mullite or tungsten shapes (FIGS. 1-9) using joining material 12. For this type of joining bodies, 10 or 14 may be ceramic (silicon carbide or mullite) or tungsten.

Joining of stainless steel, preferably 316-L, or superalloy, preferably Inconel-600 or Inconel-601, 11 over region 13 is only completed by direct joining to tungsten 3 through brazing 15 (FIGS. 10-13). This braze joining is completed after any ceramic to ceramic or ceramic to tungsten joining, since the latter is a higher temperature process than brazing. Furthermore, joining to ceramics in FIGS. 11-13 shall be as described in the previous paragraph. A joined assembly fabricated using the described method may contain as many as 2 different joint types to be described of either mixed oxide joints 12 or braze joints 15.

Combinations of silicon carbide, mullite or tungsten bodies 10 and 14 joined by this technique require only a close fit with a thin layer of joining material 12, either as a slurry or dry powder of mixed oxide 12 between the bodies. A close fit is defined as the opposing surfaces of the two bodies that are being joined having essentially the same shape so their surfaces essentially conform. The opposing surfaces do not have to be exactly the same shape. The joining material will fill any gap that may exist between the opposing surfaces. The joint gap spacing can range from 2 microns to 150 microns, but stronger joints are attained in the preferable range of 10 microns to 50 microns. The assembly is joined by heating the joining material 12 until it reaches a liquid phase for silicon carbide, mullite or tungsten to silicon carbide, tungsten or mullite joining. Many tube assembly geometries are possible, including, but not limited to, those of FIGS. 1-13.

Ceramic to ceramic joints are important as these materials cannot easily be manufactured to very long lengths or into elbows or T shaped geometries, reducing their potential application in industry, thus the need for a fabrication process such as described in the present document. The ability to join multiple sections of ceramic to achieve longer lengths and/or curved shapes greatly enhances the usability of these materials. Additionally, the joining of multiple silicon carbide, mullite and tungsten pieces onto a single silicon carbide, mullite and tungsten piece is considered. This allows, for example, the assembly of a structure consisting of a header with multiple tubes attached as in FIG. 4a. In addition, these joining methods to be described allow for the construction of a helium gas tight sealed ceramic to metal joined assembly using tungsten as a transitional coupling material from ceramic to conventional stainless steel or superalloy metal 11. Tungsten (99.95% purity) is used as a coupling for two main reasons. First, the tungsten acts as a thermal expansion grading material that manages the stresses that result from the coefficient of thermal expansion (CTE) mismatch of the low CTE ceramic and the high CTE conventional stainless steel or superalloy metal. Second, the tungsten acts as a barrier between the silicon carbide ceramics and the conventional stainless steel or superalloy metal, isolating the chemistry and preventing undesirable eutectics, specifically between silicon in the silicon carbide and nickel, cobalt or iron, at temperatures below the desired service or joining temperatures.

When joining silicon carbide, mullite or tungsten to silicon carbide, mullite or tungsten, the joining material is from a family mixed oxide materials 12, henceforth referred to as Makotite™ or Makotite™ joining material 12, designed for the purpose of joining ceramic and metal bodies for use at high service temperatures of 400° C. to 1500° C. Makotite™ is a mixed oxide joining material developed and produced by FM Technologies, Inc. Makotite™ has various formulations which are comprised of a combination of alumina ($Al_2O_3$), silica ($SiO_2$) and magnesia (MgO), with or without additions of less than 4 wt % collectively of $TiO_2$, $Fe_2O_3$, CaO, $NaO_2$, $K_2O$, $P_2O_5$ and/or any other binder or sintering aid used in the art. Makotite™ can also be made with the addition of a single or multi-modal silicon carbide powder for improved strength. The multi-modal powder is composed of a mixture of two or more silicon carbide particle sizes. Makotite™ is used as a joining material for both ceramic to ceramic and ceramic to metal joints between silicon carbide, mullite or tungsten and silicon carbide, mullite or tungsten that is preferably applied as either a slurry or dry powder 12, although applying in a more solid form such as fibers, yarn, a slab, a disk or a washer would work as well. The slurry or dry powder covers the surfaces being joined or is provided a path to do so from a reservoir once it has a reached a liquid phase.

When joining tungsten to a stainless steel or superalloy material for the purpose of transitioning back to conventional stainless steel or superalloy metal, the joining material is composed of a mixture of metals or alloys that are used to create a braze joint, applied as either a slurry or dry powder 15. As with the Makotite™ joining material 12, the slurry or dry powder 15 covers the surfaces being joined or is provided a path to do so from a reservoir once it has a reached a liquid phase.

For either mixed oxide joints 12 or braze joints 15, the powder or slurry is converted to a solid after a heating and cooling cycle, and forms a tightly bound transition layer in the joint. The degree to which the joining material in the prepared joint is heated is important to ensure a strong joint that is helium gas tight. The slurry is prepared by mixing powders with a volatile liquid binder. This allows the slurry to be applied to the parts for joining, and volatility provides the ability to remove the liquid binder before the joining cycle to prevent contamination.

Figure 6:
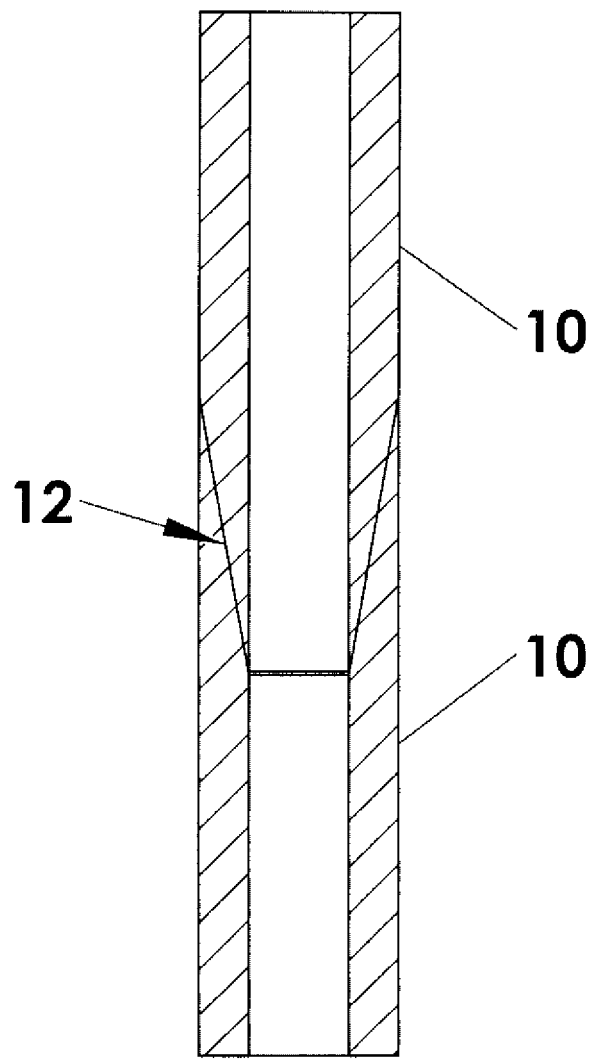
FIG. 6 is a representation of a taper joint.
Figure 7:
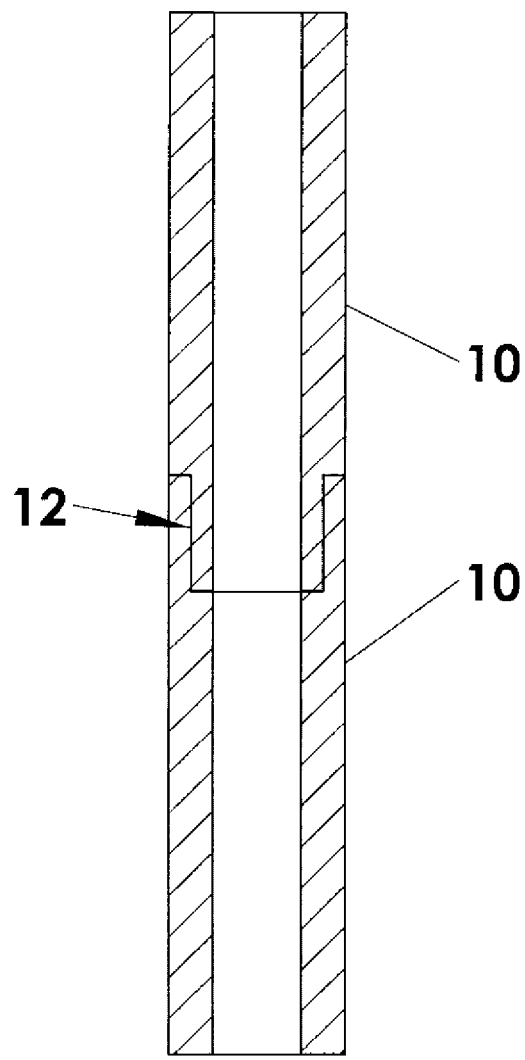
FIG. 7 is a representation of a step joint.
Figure 8:
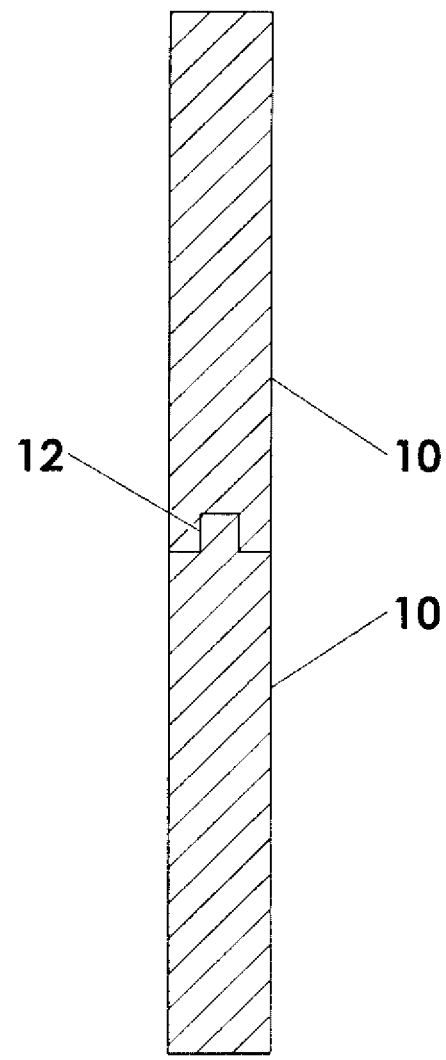
FIG. 8 is a representation of a groove joint.

To ensure that the ceramic or tungsten metal bodies 10 and 14 are aligned properly with respect to each other and to the joint, the geometry of the ceramic or tungsten metal bodies 10 and 14 may be modified by the use of a step, a groove or a taper (FIGS. 6-8).

For mixed oxide or Makotite™ joining, to provide for the joining material as a slurry or powder 12 to be in good contact with the joint interface, the geometry of the ceramic or tungsten metal bodies 10 and 14 in or near contact with the joint interface may be modified. For Makotite™ 12, a capture geometry may be devised to (1) constrain the joining material 12 in the region between the ceramic bodies 10 and 14 to be joined, and (2) provide a reservoir of joining material 12 which may wick into in the region between the ceramic or tungsten metal bodies 10 and 14 to be joined when the joining material reaches a temperature at which it can flow into the joint interface through capillary action. The capture geometry and alignment geometries may be combined, and in some cases may be identical. Makotite™ joints 12 may be achieved anywhere in the range from 1400° C. up to 1750° C.

For braze joining, to provide for the joining material as a slurry or powder 15 to be in good contact with the joint interface, the geometry of the stainless steel or superalloy 11 body and tungsten 3 body in or near contact with the joint interface may be modified. For braze joining 15, a capture geometry may be devised to (1) constrain the joining material 15 in the region between the stainless steel or superalloy 11 body and tungsten metal body 3 to be joined, and (2) provide a reservoir of joining material 15 which may wick into in the region between the stainless steel or superalloy 11 body and tungsten 3 metal to be joined when the joining material reaches a temperature at which it can flow into the joint interface through capillary action. The capture geometry and alignment geometries may be combined, and in some cases may be identical. Braze joints 15 may be achieved anywhere in the range from 700° C. up to 1350° C.

Figure 2:
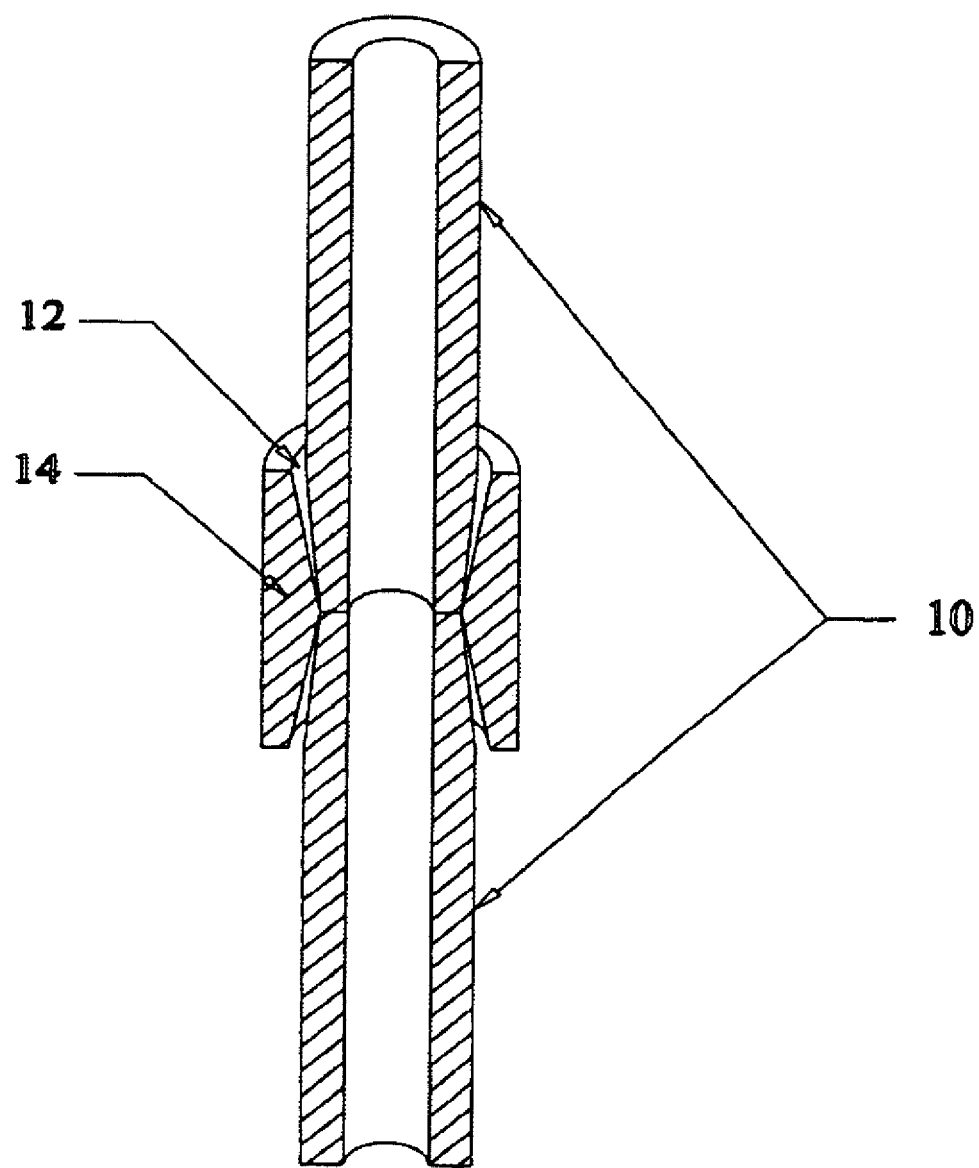
FIG. 2 is a cross-sectional view of a collar with a greater taper angle and ceramic bodies with a lesser taper angle.

To make a joint with both an alignment and capture geometry, as shown in FIG. 2, the collar 14 is machined with an inner taper that is 0.5-10 degrees halfway through on both ends of the collar 14 and the tubes 10 are machined with outer tapers that are 0-9.5 degrees at the ends that are intended to be joined. The tube 10 tapers are smaller than the collar tapers. The outer tapers at the tube 10 ends go as deep as one inner taper on the collar 14 that was machined halfway through. When the tube 10 ends are joined to the collar 14, the tapers provide alignment during heating and also a reservoir for bonding slurry 12. Because of the shallower taper angle on the tube ends compared to the collar 14, there is a volume between the tapers that acts as reservoir for the bonding slurry 12.

FIG. 1 illustrates how to make a joint without an alignment or capture geometry. The collar 14 is machined without a taper and the tubes 10 are machined without a taper at the ends where they are intended to be joined. The tubes 10 outer diameters are machined (diamond grinding bits for ceramic and conventional alumina or SiC grinding bits for tungsten or hot machining of tungsten with carbide tooling as per one skilled in the art) to be smaller than the collar inner diameter. The outer diameter of tubes 10, at the ends to be joined, is preferably machined to allow a radial difference of between 10 microns and 50 microns compared to the machined inner diameter of collar. Ball milled Makotite™ 12 must therefore end up with a powder thickness less than 50 microns in order to fill the empty space between the inner diameter of the collar 14 and the outer diameter of the tubes 10. When the tube 10 ends are joined to the collar 14, a graphite or boron nitride (h-BN) fixture may be used to maintain alignment between the tubes 10.

To make a joint with both an alignment and capture geometry, as shown in FIG. 2, the collar 14 is machined with an inner taper that is 0.5-10 degrees halfway through on both ends of the collar 14, and the tubes 10 are machined with outer tapers that are 0-9.5 degree at the ends that are intended to be joined. The tube 10 tapers are smaller than the collar tapers. The outer tapers at the tube 10 ends go as deep as one inner taper on the collar 14 that was machined halfway through. When the tube 10 ends are joined to the collar 14, the tapers provide alignment during heating, and also serve as a reservoir for bonding slurry 12. Because of the shallower taper angle on the tube ends compared to the collar 14, there is a volume between the tapers that acts as a reservoir for the bonding slurry 12. At some position the gap or spacing between the bodies will go to zero as dictated by the taper angle. The strongest joint will form in the region where the gap spacing is between 10 to 50 microns. The machining tolerance, alignment fixturing and Makotite™ 12 preparation are identical as presented in FIG. 1.

FIG. 3a illustrates how to make a joint between long pipes with different diameters. In this configuration, the collar 14, as illustrated in FIGS. 1 and 2, is now extended into a long pipe, thus defining the geometry for the joining of long pipes 10 and 14 of different diameters. The joint can be with or without an alignment or capture geometry as shown and discussed above in FIGS. 1 and 2. The machining tolerance, alignment fixturing and Makotite™ 12 preparation are identical as presented in FIGS. 1 and 2.

Figure 9:
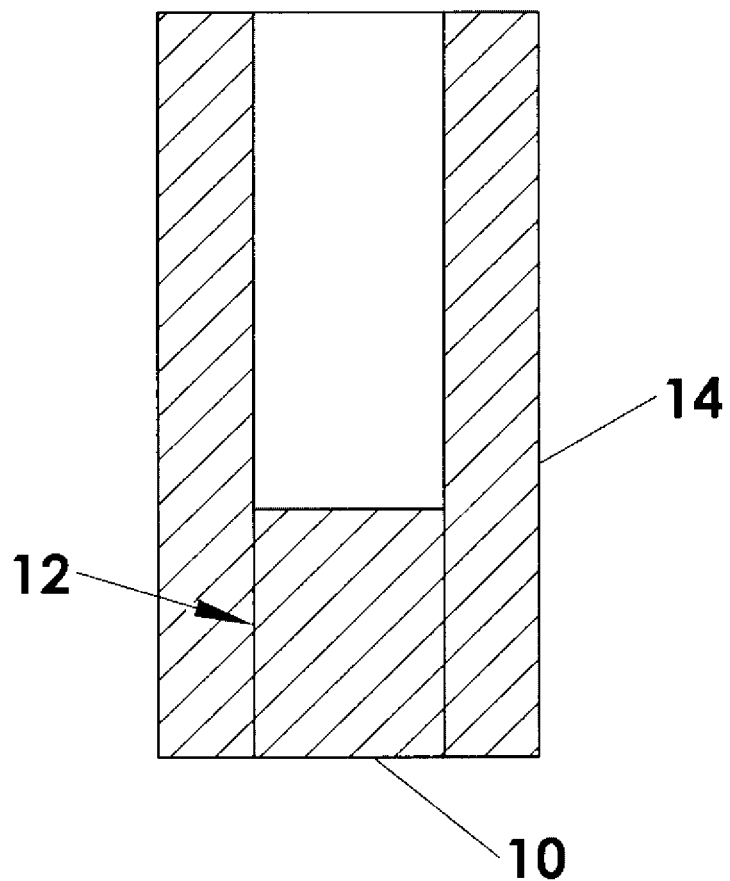
FIG. 9 is a representation of a plug joint.

FIG. 3b illustrates how to make a 90 degree elbow joint between pipes 10 and collars 14 with different diameters. In this configuration, the horizontally positioned collar 14 and horizontally positioned pipe 10 are constructed identical to that described in FIGS. 1-3a. The vertically positioned collar 14 is now machined perpendicular to its axis with or without a taper angle as previously discussed for FIGS. 1 and 2. The machining tolerance, alignment fixturing and Makotite™ preparation are identical as presented in FIGS. 1 and 2. To close either or both the top and bottom openings of the vertically positioned collar 14, a plug joint can be completed as illustrated in FIG. 9. The machining tolerance, alignment fixturing and Makotite™ 12 preparation are identical as presented in FIGS. 1 and 2.

FIG. 3c illustrates how to make a 180 degree U-joint between pipes 10 and collars 14 with different diameters. The same procedure is followed as explained in FIGS. 1-3b and 9. The machining tolerance, alignment fixturing and Makotite™ 12 preparation are identical as presented in FIGS. 1 and 2.

FIG. 3d illustrates how to make Y-junction joints with arbitrary angle between the pipes 10 and collar 14 with different diameters. In this case, the collar 14 starts out as a block of ceramic or tungsten metal, and is machined as described in FIGS. 1-2 to become hollow so as to allow pipes 10 to transmit fluids or gases between them. Alternatively, the block, if ceramic may be formed hollow in the green state (as per one experienced in the art) or if tungsten metal may be formed hollow (as per one experienced in the art) and in either case require only slight machining to form the proper tolerance (as discussed previously in FIGS. 1-2) collar 14. All joining is as discussed in FIGS. 1-3c, and 9 if extra holes need to be filled. The machining tolerance, alignment fixturing and Makotite™ 12 preparation are identical as presented in FIGS. 1 and 2.

Figure 4A:
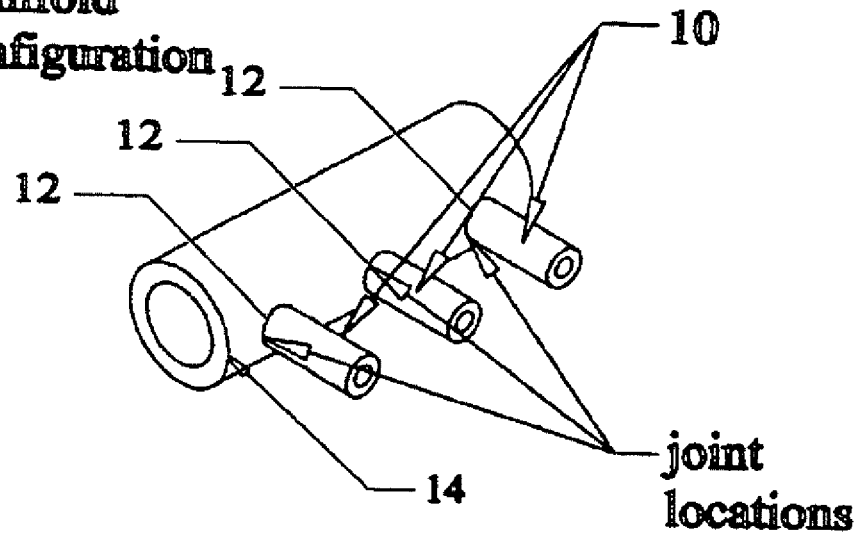
FIG. 4a is a perspective view of a large pipe connected to smaller pipes.

FIG. 4a illustrates how to make a manifold of joined pipes 10 with a much large diameter collar 14. In this configuration, the pipes are all in a line, but may be at arbitrary angles with respect to the collar 14. FIG. 4a is an extension of FIGS. 3c and 3d. All joining is as discussed in FIGS. 1-3c, and 9 if extra holes need to be filled. The machining tolerance, alignment fixturing and Makotite™ 12 preparation are identical as presented in FIGS. 1 and 2. Furthermore, the collar may have a round, square or rectangular cross-section that is hollow and/or have closed ends, and may be ceramic or metal or tungsten, as described herein.

Figure 4B:
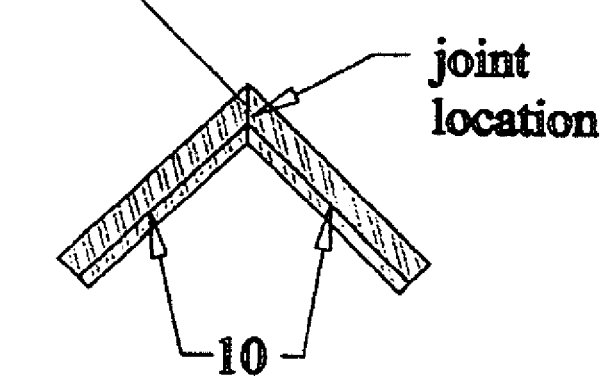
FIG. 4b is a perspective view of a corner.

FIG. 4b illustrates how to make a 90 degree corner between two plates 10 with Makotite™ 12. Instead of a 90 degree angle, the angle may of course be of arbitrary value. Illustrated is the simplest geometry of two plates 10 machined flat at an angle of 45 degrees, then butt joined together to produce a 90 degree corner. Machining methods are as discussed in FIGS. 1-2, except now a flat surface is desired. Flatness should preferably be within 50 microns. The alignment fixturing and Makotite™ preparation are identical as presented in FIGS. 1 and 2. Instead of a butt joint between two flat faces, the faces may be matching male and female saw teeth or square teeth (see FIG. 8) to achieve more joining surface area for a stronger joint.

Figure 5:
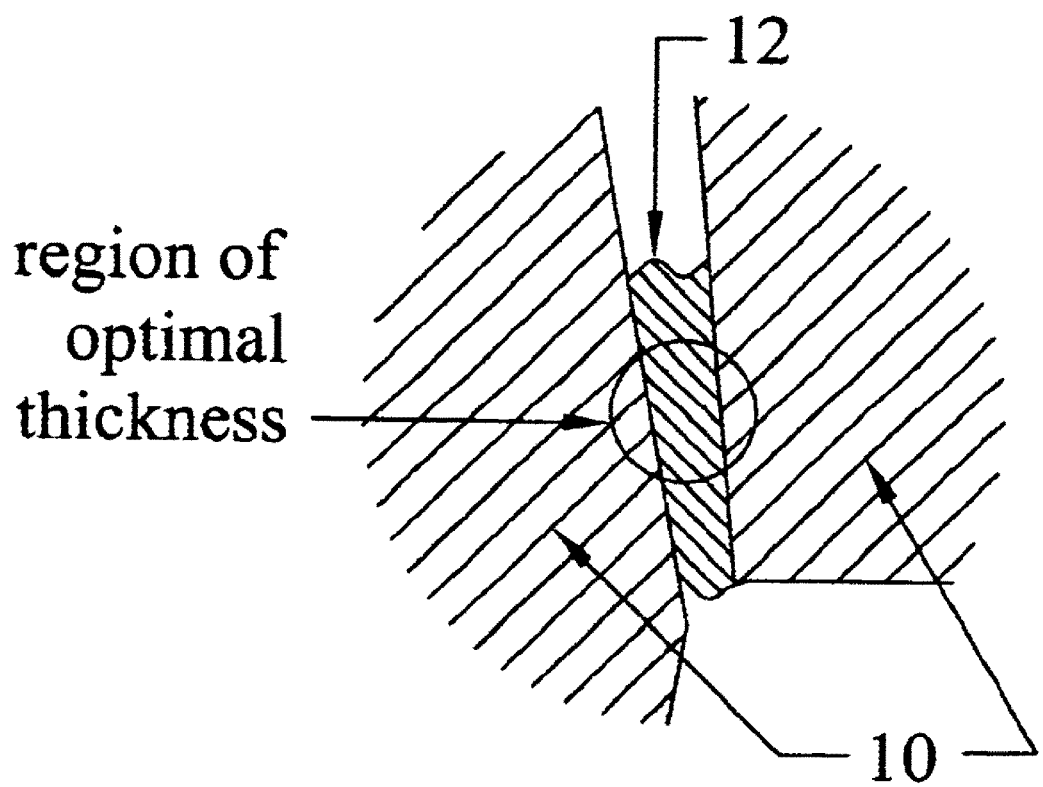
FIG. 5 is a representation of a joint.

FIG. 5 illustrates in more detail the joining of two bodies 10 with Makotite™ 12. If the joint becomes too thin, then the Makotite™ 12 may not reach the desired faces to be joined. Alternatively, if the joint spacing is too large, then the strength of the joint depends more on the volumetric strength of the Makotite™ 12 rather than the surface forces between the Makotite™ 12 and the body 10.

FIGS. 6-8 illustrates taper, step and groove joining of bodies 10 without collars 14. The same procedures, along with machining, machining tolerances, Makotite™ 12 preparation and fixturing, are the same as discussed in FIGS. 1-4b.

FIG. 9 illustrates how to make a plug 10 and a collar 14 joint using Makotite™ 12, with the sole purpose of closing the end of an open structure and achieving a helium gas tight seal. The plug 10 in this case is a solid rod or of a shape that closely matches the opening of a collar 14 which may be circular, square or of arbitrary shape or angle. Plug 10 may be machined from a plate of ceramic or tungsten metal to fill the space to the inner wall of collar 14, with the tolerance schedule previously described in FIGS. 1-2. This type of plug joint may be used in FIGS. 1-4a, 6 and 7 to close one or more openings. Illustrated is a zero degree mating joint, as in FIG. 1; however, it may be useful to create taper joints as shown in FIG. 2 or 6, or a step joint as in FIG. 7. Once fixed in place, this joint forms independent of its orientation with respect to the direction of the gravitation vector.

Figure 10:
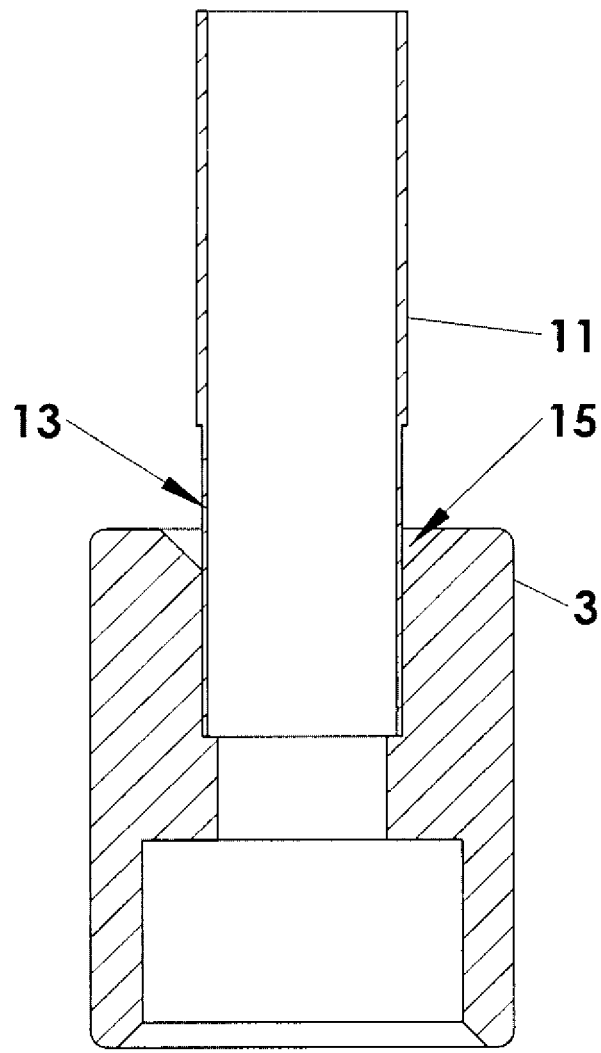
FIG. 10 is a representation of a braze joint.

FIG. 10 illustrates how to make a braze joint between a collar of tungsten 3 and a tube of either stainless steel or superalloy 11. In this configuration, the collar is made specifically from tungsten 3 and extended over or within a long pipe of stainless steel or superalloy 11. The joint can be with or without an alignment or capture geometry, as shown and discussed above in FIGS. 1 and 2. The tube 11 outer or inner diameter, depending on the desired joint configuration, is always machined to be an interference or taper fit with the collar inner or outer diameter. A braze alloy 15, to be described below, is placed in, around or against the joining area after the parts are fit together.

FIG. 11 illustrates a ceramic to metal transition that contains both a Makotite™ joint 12 and a brazed joint 15. Here, a silicon carbide 1 or mullite 2 tube is joined to a transitional tungsten collar 3 using Makotite™ 12, as described in FIGS. 1 and 2. A stainless steel or superalloy 11 tube is then brazed 15 to the tungsten collar 3 as described in FIG. 10 to complete the ceramic to metal transition.

Figure 13:
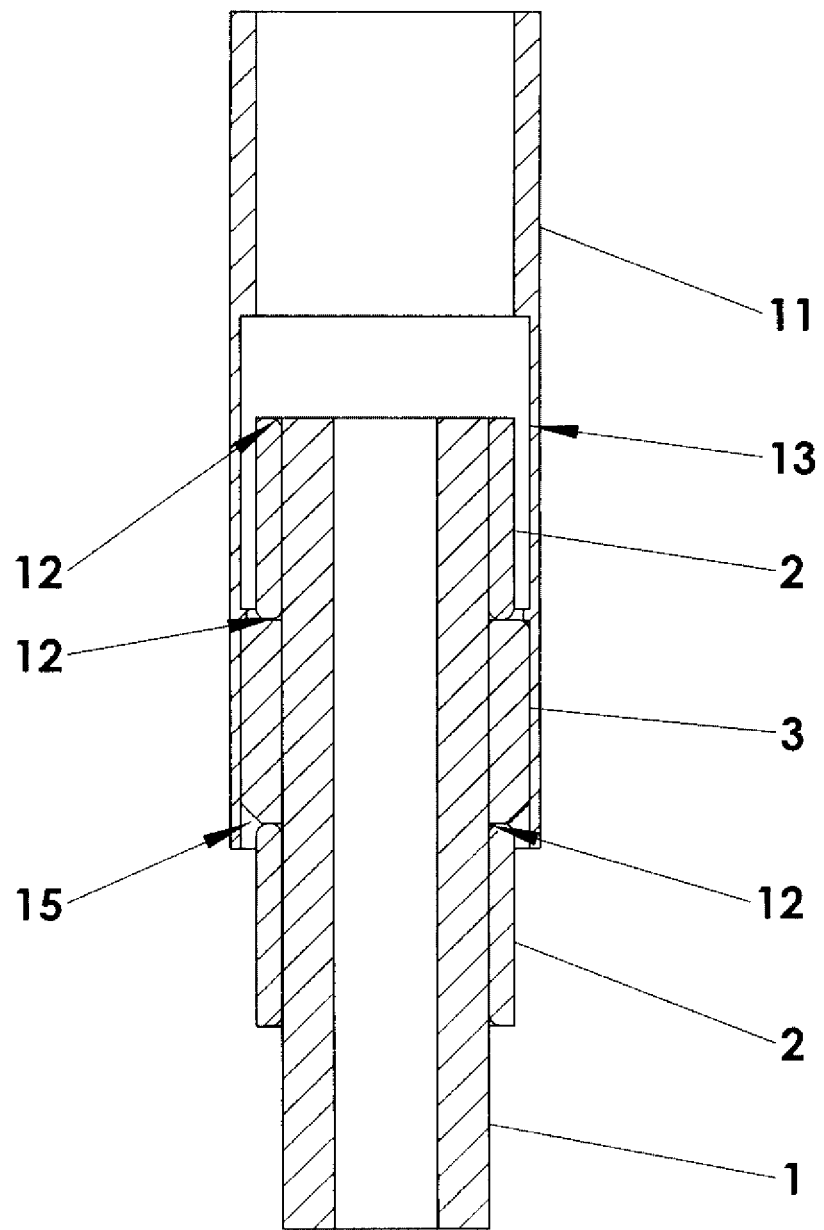
FIG. 13 is a representation of the alternative ceramic to metal joint configuration.
Figure 14:
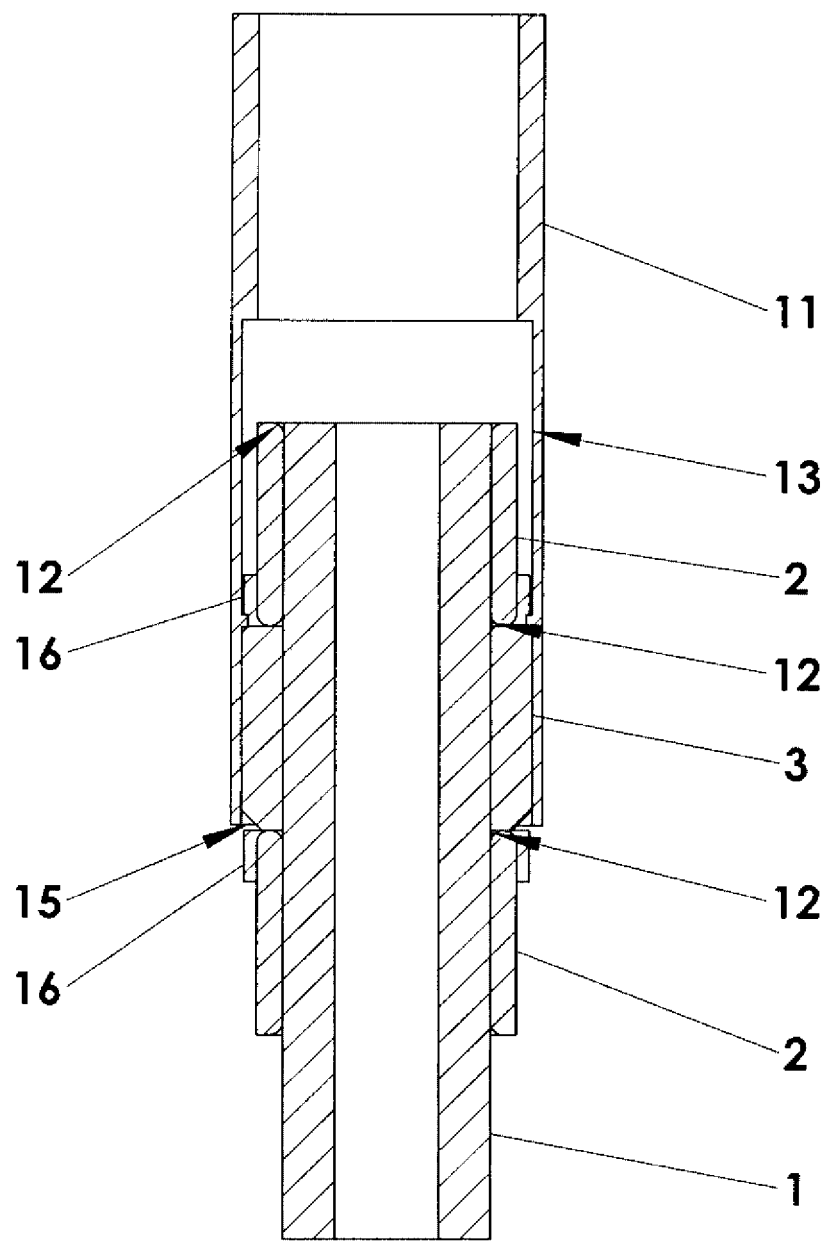
FIG. 14 is a representation of the alternative ceramic to metal joint configuration with added oxidation protection.

FIG. 12 illustrates an example tungsten coupling 3. The coupling shown in FIG. 12 is for a ceramic to metal transition configuration as described above for FIGS. 10 and 11. Tungsten couplings 3 can also be in the form of a sleeve, as shown in FIGS. 13 and 14. For the ceramic to metal transition with the tungsten coupling 3 as a sleeve, silicon carbide 1 or mullite 2 is joined to either the ID or OD of the tungsten sleeve 3 with a Makotite™ joint 12, and stainless steel or superalloy 11 is joined to either the OD or the ID of the tungsten sleeve 3 with a braze joint 15, where the tungsten sleeve 3 is both a coupling and a barrier between the silicon carbide 1 or mullite 2 and the stainless steel or superalloy 11. The tungsten coupling may be used with or without the implementation of an oxidation protective coating 34.

As mentioned, this technology makes use of up to 2 distinct joint types, mixed oxide joints 12 and braze joints 15. For the mixed oxide joints using Makotite™ joining material, although various Makotite™ formulations can be produced, there are 2 formulation that are preferred for ceramic to ceramic and ceramic to metal joints that is, between silicon carbide, mullite or tungsten and silicon carbide, mullite or tungsten. The first formulation involves a mixture of between 30 wt % (weight percent or percent by mass) and 80 wt %, nominally 60 wt %, aluminum-silicate, also known as Lava or Wonder Stone, and between 20 wt % and 70 wt %, nominally 40 wt %, magnesium-silicate, also known as Steatite. The aluminum-silicate and magnesium-silicate are mixed in powder form to a 100% weight fraction to form Makotite™. The second formulation, using powders, involves a mixture of between 16.8 wt % and 35.8 wt %, nominally 28.2 wt %, alumina (99.8% purity), between 57.9 wt % and 61.2 wt %, nominally 59.2 wt %, silica (99.99% purity) and between 6.3 wt % and 22.0 wt %, nominally 12.6 wt %, magnesia (99+% purity). The alumina, silica and magnesia are mixed in powder form to a 100% weight fraction to form Makotite™. When mixing powders, any particle size from 150 microns down to nanometer scale particles, or combination thereof, are acceptable for the constituent materials of any Makotite™ formulation.

The powders can be used as is in this basic mixture, but it is preferable to mill the powder mixture using a planetary ball mill for between 4 and 12 hours. Once prepared, the Makotite™ joining material is applied as a slurry or dry powder that covers the surfaces being joined, or is provided a path to do so from a reservoir once it has a reached a liquid phase, with a volume of joining material that is greater than or equal to the volume of empty space present between the surfaces to be joined when assembled prior to application of the joining material. If a slurry is the desired form of application, the slurry is created by mixing the prepared Makotite™ powder with a volatile liquid binder such as water or alcohol that is allowed to evaporate as the joint assembly is heated. Once sufficient joining material has been applied in and/or around the joint area, fixturing is applied to hold the coupled parts together prior to heating. The type and level of fixturing is dependent on the size and configuration of parts to be joined. Examples of fixturing used are gravity, if the parts overlap and are able stand in a stable manner once assembled, or graphite sleeves that are shaped to match the parts and removed after joining is complete or, in the case of long parts greater than 0.5 m in length, gripping the parts outside of the heating area using something such as a Wilson seals that act to hold the assembly together. Once parts are assembled and fixed, the joint is heated, either radiantly or using microwaves and in either vacuum or an inert gas atmosphere, to between 1400° C. and 1600° C. for the aluminum-silicate/magnesium-silicate or to between 1550° C. and 1750° C. for the alumina/silica/magnesia formulation, to allow the joining material to achieve a liquid phase. Once heated, the joint is held at temperature for between 1 minute and 5 minutes to allow the joining material to spread evenly within the joint area. The joint is then allowed to cool to room temperature, and is ready to either be joined to other ceramic or metal parts or be used as part of a furnace coil assembly.

Braze joints 15 are used to join tungsten 3 to a superalloy material 11, such as Inconel-600, for the purpose of transitioning to conventional metal, with the conventional metal being weldable to the superalloy material through standard welding techniques. The preferred joining material, applied as either a slurry or dry powder 15, is a mixture of 10 wt %-80 wt % 80/20 nickel-chromium alloy powder, also known as Nichrome V, and 20 wt %-90 wt % copper wire or grain of ≥99.99% purity. The best resultant alloy is nominally 33 wt % of 80/20 nickel-chromium alloy and 67 wt % copper. The order of assembly is as follows. First the superalloy tube 11 is interference fit to the tungsten tube 10 to create an air tight seal. To minimize stresses and prevent cracking of the tungsten tube, prior to insertion into the tungsten, for a tungsten mating wall thickness of 0.25 in. or greater, the superalloy tube must be machined to reduce its wall thickness 13 to between 0.020 in and 0.040 in (thinning is generally less than 20% of the tungsten wall thickness) over a length equal to or greater than the insertion length plus the diameter of the tube being inserted. Next, the copper wire or grain is placed between the superalloy and tungsten tubes in a capture groove 15 or angled joint, such as in FIG. 10. Finally, the nickel-chromium alloy powder is packed on top of the copper wire or grain. This joint is then heated to 800° C. in vacuum, at which point an atmosphere of inert gas such as Argon gas is added and the temperature is raised to 1200° C. for 1-5 minutes. The assembly is then allowed to cool to room temperature. This arrangement forms a graded layer where most of the copper at the bottom of the joint is alloyed with nickel-chromium. From the bottom to the top of the joint, the concentration of the braze alloy goes from primarily copper at the bottom to primarily nickel-chromium at the top, in this way forming a helium gas tight joint with ductility and oxidation resistance to over 1000° C. However, without additional oxidation protection applied to any exposed tungsten, the joined tungsten to superalloy assembly is limited in service temperature to 400° C. due to the oxidation behavior of the base tungsten material. If the service temperature allows for a lower temperature braze joint, any ductile oxidation resistant braze alloy with a liquidus temperature as low as 500° C. may be used in place of the copper-nickel-chromium braze alloy described above. Higher temperature oxidation resistant brazes up to about 1350° C. may be used, but certainly the braze melting temperature must be below the melting temperature of the superalloy or stainless steel unless it is desired to cast (as per one experienced in the art) the superalloy or stainless steel directly to the tungsten.

For ceramic to metal joined system applications where service temperatures of greater than 400° C. are desired for the ceramic portion, the ceramic to metal transition must be extended beyond all hot zones of greater than 400° C., and also be extended far enough such that any hot liquid or gas flowing in or around the ceramic to metal transition has cooled sufficiently to prevent the ceramic to metal transition from reaching temperatures greater than 400° C., to avoid ceramic to metal joint failure due to excessive tungsten oxidation. For the case of hot liquids or gases flowing through joined lengths of pipe, methods to reduce the length of additional structure needed, such as using a manifold to divert flow to many much smaller diameter tube sections of ceramic pipe for the purpose of more rapid thermal cooling over a much shorter length, can be used.

If the ceramic to metal transition cannot be extended beyond all hot zones of greater than 400° C. or if the ceramic to metal transition is desired to be at a service of greater than 400° C., additional oxidation protection 17 must be provided to any exposed tungsten material, i.e. tungsten surfaces not coated or sealed from exposure to oxidizing atmospheres with oxide joining material, silicon carbide or mullite. Reactive evaporation, evaporation, sputtered, melted and/or plating of chromium may be used to apply a first level of high temperature (400° C. to 700° C.) oxidation protection 17 to the exposed tungsten. Reactive evaporation is preferred as it will provide an overlay of material across the interface of the exposed tungsten and the oxide joining material, silicon carbide or mullite. Plating alone could leave the tungsten vulnerable at these interlaces. Note that the reactive evaporation may also be performed on tungsten pieces prior to joining to silicon carbide or mullite if a configuration such as that show in FIG. 11, where a tungsten sleeve is placed around a silicon carbide or mullite tube between two silicon carbide or mullite sleeves with all three sleeves joined to the silicon carbide or mullite tube using Makotite™. This capture geometry is necessary to form an air tight seal between the ceramic, chromium coated tungsten and Makotite™ joining materials.

Reactive evaporation, in this case, takes advantage of the relatively high vapor pressure of chromium ranging from 1×10-5 torr to 0.1 torr at temperatures below the temperature of the mixed oxide joining operation of 1400-1750° C. To perform the reactive evaporation, the tungsten part or assembly is immersed in chromium powder or pellets with the assistance of a graphite or h-boron nitride crucible or form. Once prepared, the powder immersed part or assembly is heated, either radiantly or using microwaves or any other means of heating, to between 1100° C. and 1400° C. in vacuum and held at temperature for 10 minutes to 1 hour to allow the chromium powder to evaporatively coat the tungsten part or assembly. Having both the chromium powder and tungsten part or assembly at elevated temperature allows for a more strongly bonded evaporative coating. The joint is then allowed to cool to room temperature. A 20-100 micron thick layer of chromium is formed in 30 minutes at 1250° C. Remaining chromium bulk must be removed before any plating process is performed; this is done by scraping of the excess chromium. The chromed assembly is now good for use up to about 700° C.

Additional oxidation protection can be achieved through conventional electroplating techniques, preferably plating alternating layers of nickel followed by chromium with nickel to chromium layer thickness ratios of 4 to 1, to achieve a 25 micron to 250 micron final oxidation resistant coating. Due to nickel having a density about 20% higher than that of chromium, a film that is approximately 80 wt % nickel and 20 wt % chromium is achieved by plating alternating layers of nickel followed by chromium with a nickel to chromium layer thickness ratio of 4 to 1. Electroless nickel plating may also be applied in place of conventional electroplating to achieve this final 25 micron to 250 micron oxidation resistant coating. Nickel or nickel-chromium alloys, $Ni_xCr_y$, may also be applied by reactive evaporation or plating after application of the initial chromium layer to improve oxidation resistance further. These additional protections all serve to improve oxidation resistance of the ceramic to metal transition to up to about 1000° C.

Another step that may be taken to improve the ceramic to metal joint for improved oxidation resistance is to implement metalized mullite. For this, prior to joining mullite 2 to tungsten 3 with Makotite™, mullite sleeves 2 are prepared for the process of providing further oxidation resistance beyond the first level of chromium coated tungsten. First, a 3 to 10 micron layer of tungsten is sputtered onto the outer surfaces of the mullite sleeves 2 to improve adhesion of the sintered coating that is to follow. The material for the sinter coating is prepared by mixing between 97 wt % and 99 wt %, nominally 98.3 wt %, tungsten powder and between 1 wt % and 3 wt %, nominally 1.7 wt %, silicon powder. The mixed tungsten-silicon powder is ball milled for between 10 and 14 hours. Graphite or h-boron nitride crucibles are made to hold the mullite sleeves 2, while also providing a radial and axial air gap of between 0.08 in. and 0.16 in. to allow for the tungsten-silicon powder to form a collar 16 around the mullite 2. The powder immersed mullite parts are heated radiantly to 1050° C. in vacuum, and then to 1600° C. in argon. The parts are held at 1600° C. for one hour to allow the tungsten-silicon powder to sinter itself around the mullite sleeves 2. Once cooled, the collared sleeves are removed from the crucible and the tungsten-silicon sintered collars 16 are ground smooth to a thickness of between 0.020 in. and 0.060 in. using abrasive tooling. The sintered tungsten-silicon collars 16 are now bonded to the mullite sleeves 2. At this point, the metalized mullite 2 is now ready for joining to silicon carbide 1 and tungsten 3 with Makotite™ joining material. After the Makotite™ joining step, the sintered tungsten-silicon collars 16 and tungsten are wrapped with a single layer of 0.005 in. thick 80/20 nickel-chromium alloy foil. The foil wrapped parts are then placed on a graphite stand and heated radiantly to 1425° C. in argon to allow the foil to melt and coat the tungsten and sintered tungsten-silicon collars 16 and to densify the sintered tungsten-silicon collars 16. The joined assembly is now ready for additional oxidation protection by means of conventional electroplating, as described above.

Using this described joining technology, every ceramic to ceramic and ceramic to metal joint is helium leak tight to less than 1×10-9 torr.-L./sec. helium leak rate, and oxidation resistant, with service temperature from 1100-1500° C. for ceramic to ceramic and 400-1000° C. for ceramic to metal. The joints have strengths comparable to the as received materials. For ceramic to ceramic joints, flexural strength is 334 MPa and shear strength is 241 MPa. For ceramic to metal joints, shear strength is greater than 308 MPa.

EXAMPLES

FIGS. 1-12 display a variety joint configurations. Silicon carbide, mullite or tungsten to silicon carbide, mullite or tungsten butt joints, sleeve joints, step joints, taper joints, groove joints and plug joints have all been made using Makotite™ joining material. All of these joint configurations are helium leak tight. In FIG. 5, the joint was deliberately shown with a wide gap for viewing the joint. Note that the joint gap can be made with nearly zero thickness.

Example 1

Makotite™ joining material is first prepared by mixing 14.120 g alumina powder of 500 mesh grain size, 7.595 g silica powder of 500 mesh grain size and 6.285 g magnesia powder of 500 mesh grain size. The mixed Makotite™ powder is placed in a 100 mL alumina ceramic grinding jar with 100 6 mm diameter alumina ceramic grinding balls and 16 10 mm diameter alumina ceramic grinding balls. The jar is then sealed, loaded into a planetary ball mill and allowed to mill for 8 hours. Once ball milling is completed, the Makotite™ powder is removed from the jar and separated from the alumina grinding balls using a sieve.

Two silicon carbide tubes measuring 2.375 in. OD×2 in. ID×6 in. long are prepared for joining by machining using diamond based abrasive grinding bits such that one tube has a male step and the other a female step of 0.5 in length, as shown in FIG. 7, with a gap of 0.0015 in between the OD of the male step and the ID of the female step.

A slurry is then created by mixing 5 g of the milled and sieved Makotite™ powder with ethanol until a viscosity similar to that of paint is achieved, approximately 10 cP. The slurry is applied between the faces of the steps to be joined 12. Once a layer of slurry of 0.010 in thickness has been applied in and around the joint area, the female tube is inserted into the male tube and the excess joining material from the radial faces is allowed to collect between the butting faces of the tubes. Graphite fixturing is applied such as to provide a stable base, allowing the assembly to stand vertically as shown in FIG. 7 and a 50 g weight to be placed on top of the assembly to prevent the joint from opening once the joining material has reached a liquid phase upon heating. Once parts are assembled and fixed, the joint assembly is heated radiantly in vacuum to 1050° C. at 5° C. per minute, at which point 1 atmosphere of argon is vented into the furnace. It is preferable to begin the process in vacuum to assist in removing any excess water vapor, unwanted organics, or any other volatiles that may have been introduced in the preparation process. Once in argon, the joint assembly is further heat to 1725° C. at 5° C. per minute to allow the joining material to achieve a liquid phase, and held at 1725° C. for 3 minutes to allow the joining material to spread evenly within the joint area. An atmosphere of argon, or another inert gas, is necessary above 1400° C. to prevent excessive vaporization of SiO2 from the joining material. The joint assembly is then allowed to cool to room temperature at 5° C. per minute to complete the joining process.

Example 2

Makotite™ joining material is first prepared by mixing 30 g aluminum-silicate powder of 2500 mesh grain size and 20 g magnesium-silicate powder of 325 mesh grain size. The mixed Makotite™ powder is placed in a 100 mL alumina ceramic grinding jar with 100 6 mm diameter alumina ceramic grinding balls and 16 10 mm diameter alumina ceramic grinding balls. The jar is then sealed, loaded into a planetary ball mill and allowed to mill for 6 hours. Once ball milling is completed, the Makotite™ powder is removed from the jar and separated from the alumina grinding balls using a sieve.

A 1.25 in. OD×0.946 in. ID×3 in. long tungsten tube and a 1 in. OD×0.5 in long silicon carbide plug are prepared for joining by machining using diamond based abrasive grinding bits such that the tungsten tube has a 3° ID taper at one end that opens to a 1 in. ID at the mouth of the tube and the silicon carbide plug has a 3° OD taper along its entire length that such that one end of the plug retains its original 1 in. OD. When assembled as shown in FIG. 9, this will result in a 0.0016 in. gap for joining material to flow and fill between the OD of the silicon carbide plug and the ID of the tungsten taper.

A slurry is then created by mixing 5 g of the milled and sieved Makotite™ powder with ethanol until a viscosity similar to that of paint is achieved, approximately 10 cP. The slurry 12 is applied on the ID of the tapered portion of the tungsten tube and the OD of the silicon plug. Once a layer of slurry of 0.010 in thickness has been applied in and around the joint area, the silicon carbide plug is inserted into the tapered end of the tungsten and the excess joining material from the radial faces is allowed to collect on the face of the silicon carbide plug that is inside the tungsten tube. Excess powder from the outward face of the silicon carbide plug is wiped off using an alcohol wipe. The prepared joint assembly is placed on a boron nitride base such that it stands vertically, as shown in FIG. 9, allowing the tungsten to act as a weight at the top of the assembly to prevent the joint from opening once the joining material has reached a liquid phase upon heating. Once parts are assembled and fixed, the joint assembly is heated radiantly in vacuum to 1200° C. at 5° C. per minute, at which point 1 atmosphere of argon is vented into the furnace. It is preferable to begin the process in vacuum to assist in removing any excess water vapor, unwanted organics, or any other volatiles that may have been introduced in the preparation process. Once in argon, the joint assembly is further heat to 1540° C. at 5° C. per minute to allow the joining material to achieve a liquid phase, and held at 1540° C. for 3 minutes to allow the joining material to spread evenly within the joint area. The joint is then allowed to cool to room temperature at 5° C. per minute to complete the joining process.

Example 3

Makotite™ joining material is first prepared by mixing 30 g aluminum-silicate powder of 2500 mesh grain size and 20 g magnesium-silicate powder of 325 mesh grain size. The mixed Makotite™ powder is placed in a 100 mL alumina ceramic grinding jar with 100 6 mm diameter alumina ceramic grinding balls and 16 10 mm diameter alumina ceramic grinding balls. The jar is then sealed, loaded into a planetary ball mill and allowed to mill for 6 hours. Once ball milling is completed, the Makotite™ powder is removed from the jar and separated from the alumina grinding balls using a sieve.

As shown in FIG. 13, a silicon carbide tube 1 measuring 1.013 in. OD×0.5004 in. ID×6 in. long is machined using diamond grinding bits so that the final OD is 1.000 in. Three sleeves, two are mullite 2 and one is tungsten 3 with the middle sleeve being tungsten 3, the ID of all three sleeves are diamond ground so as to achieve a final ID of between 1.002 in. The sleeves of mullite 2 have an OD of 1.25 in. and a length of 1 in. The mating mullite 2 and tungsten 3 faces are diamond ground to a flatness of less than 0.001 in. The tungsten sleeve 3 has an OD of 1.401 in. to allow for an interference fit of the Inconel 600 tube 11. The initial size of the Inconel 600 tube 11 is 1.500 in. OD×1.250 in. ID×4.125 in. long. The Inconel 600 tube 11 is then machined to reduce its wall thickness 13 to an ID of 1.400 in. over a length of 2.625 in., leaving a small nipple 0.010 in. high×0.020 in. long beginning at a depth of 1.118 in. to prevent the tungsten 3 from inserting further than distance of 1.118 in. from the end of the Inconel 600 tube 11.

Prior to joining, the tungsten sleeve 3 is given first level oxidation protection through reactive evaporation of chromium. For this, a graphite crucible is made to hold the tungsten sleeve 3, while also providing a radial and axial air gap of 0.080-0.0120 in. to allow for chromium powder to immerse the sleeve. The powder immersed part is heated radiantly to 1250° C. in vacuum and held at temperature for 30 minutes to allow the chromium powder to evaporatively coat a 50 micron thick layer onto the tungsten sleeve 3. Once cooled, the sleeve is removed from the crucible and the remaining chromium bulk is removed by scraping of the excess chromium.

Makotite™ joining material is then prepared as a slurry by mixing 5 g of the milled and sieved Makotite™ powder with ethanol until a viscosity similar to that of paint is achieved, approximately 10 cP. The slurry 12 is applied between the mating faces of mullite 2 and tungsten 3. The Inconel tube 11 is not being joined yet. Once a layer of slurry 12 of 0.010 in thickness has been applied in and around the joint area, graphite fixturing is applied such as to prevent the mullite sleeves 2 and tungsten sleeve 3 from sliding down from gravity. Once parts are assembled and fixed, the joint assembly is heated radiantly in vacuum to 1200° C. at 5° C. per minute, at which point 1 atmosphere of argon is vented into the furnace. It is preferable to begin the process in vacuum to assist in removing any excess water vapor, unwanted organics, or any other volatiles that may have been introduced in the preparation process. Once in argon, the joint assembly is further heat to 1540° C. at 5° C. per minute to allow the joining material to achieve a liquid phase, and held at 1540° C. for 3 minutes to allow the joining material to spread evenly within the joint area. The joint is then allowed to cool to room temperature at 5° C. per minute, at which point this subassembly is now ready for joining the tungsten circumference to the Inconel tube 11.

For this next step, the Inconel-600 tube is first interference fit to the tungsten sleeve 3 to create a seal. Then, with the assembly standing vertically such that the Inconel tube is at the bottom, a ring of 1 mm diameter copper wire is placed between the superalloy 11 and tungsten 3 tubes in a capture groove 15, such as in FIG. 13. Finally, the nickel-chromium alloy powder is packed on top of the copper wire. This joint is then heated to 800° C. in vacuum, at which point an atmosphere of inert gas such as Argon gas is added and the temperature is raised to 1200° C. for 1-5 minutes. The assembly is then allowed to cool to room temperature to complete the joining process. The joined assembly, as shown in FIG. 13, is now a complete helium gas tight and strong component ready to be used to a service temperature of up to 700° C.

Example 4

Makotite™ joining material is first prepared by mixing 30 g aluminum-silicate powder of 2500 mesh grain size and 20 g magnesium-silicate powder of 325 mesh grain size. The mixed Makotite™ powder is placed in a 100 mL alumina ceramic grinding jar with 100 6 mm diameter alumina ceramic grinding balls and 16 10 mm diameter alumina ceramic grinding balls. The jar is then sealed, loaded into a planetary ball mill and allowed to mill for 6 hours. Once ball milling is completed, the Makotite™ powder is removed from the jar and separated from the alumina grinding balls using a sieve.

As shown in FIG. 14, a silicon carbide tube 1 measuring 1.013 in. OD×0.5004 in. ID×6 in. long is machined using diamond grinding bits so that the final OD is 1.000 in. Three sleeves, two are mullite 2 and one is tungsten 3 with the middle sleeve being tungsten 3, the ID of all three sleeves are diamond ground so as to achieve a final ID of between 1.002 in. The sleeves of mullite 2 have an OD of 1.25 in. and a length of 1 in. The mating mullite 2 and tungsten 3 faces are diamond ground to a flatness of less than 0.001 in. The tungsten sleeve 3 has an OD of 1.401 in. to allow for an interference fit of the Inconel 600 tube 11. The initial size of the Inconel 600 tube 11 is 1.500 in. OD×1.250 in. ID×3.975 in. long. The Inconel 600 tube 11 is then machined to reduce its wall thickness 13 to an ID of 1.400 in. over a length of 2.475 in., leaving a small nipple 0.010 in. high×0.020 in. long beginning at a depth of 0.968 in. to prevent the tungsten 2 from inserting further than distance of 0.968 in. from the end of the Inconel 600 tube 11.

Prior to joining, the tungsten sleeve 3 is given first level oxidation protection through reactive evaporation of chromium. For this, a graphite crucible is made to hold the tungsten sleeve 3, while also providing a radial and axial air gap of 0.080-0.0120 in. to allow for chromium powder to immerse the sleeve. The powder immersed part is heated radiantly to 1250° C. in vacuum and held at temperature for 30 minutes to allow the chromium powder to evaporatively coat a 50 micron thick layer onto the tungsten sleeve 3. Once cooled, the sleeve is removed from the crucible and the remaining chromium bulk is removed by scraping of the excess chromium.

Prior to joining, the mullite sleeves 2 are prepared for the process of providing further oxidation resistance beyond the first level of chromium coated tungsten. First, a 3 micron layer of tungsten is sputtered onto the outer surfaces of the mullite sleeves 2 that are to be in contact with the silicon carbide tube 1 and tungsten sleeve 3 to improve adhesion of the sintered coating that is to follow. The material for the sinter coating is prepared by mixing 49.15 g tungsten powder of 4800 mesh grain size and 0.85 g silicon powder of 100 mesh grain size. The mixed tungsten-silicon powder is placed in a 100 mL alumina ceramic grinding jar with 100 6 mm diameter alumina ceramic grinding balls and 16 10 mm diameter alumina ceramic grinding balls. The jar is then sealed, loaded into a planetary ball mill and allowed to mill for 12 hours. Once ball milling is completed, the mechanically alloyed tungsten-silicon powder is removed from the jar and separated from the alumina grinding balls using a sieve. Next, graphite crucibles are made to hold the mullite sleeves 2, while also providing a radial and axial air gap of 0.118 in. to allow for the tungsten-silicon powder to form a collar 16 around the mullite 2. The powder immersed mullite parts are heated radiantly to 1050° C. in vacuum, and then to 1600° C. in argon. The parts are held at 1600° C. for one hour to allow the tungsten-silicon powder to sinter itself around the mullite sleeves 2. Once cooled, the collared sleeves are removed from the crucible and the tungsten-silicon sintered collars 16 are ground smooth to a thickness of 0.040 in. using abrasive tooling. The sintered tungsten-silicon collars 16 are now bonded to the mullite sleeves 2. At this point, the metalized mullite 2 is now ready for joining to silicon carbide 1 and tungsten 3 with Makotite™ joining material.

Makotite™ joining material is then prepared as a slurry by mixing 5 g of the milled and sieved Makotite™ powder with ethanol until a viscosity similar to that of paint is achieved, approximately 10 cP. The slurry 12 is applied between the mating faces of collared mullite 2 and tungsten 3. The Inconel tube 11 is not being joined yet. Once a layer of slurry of 0.010 in thickness has been applied in and around the joint area, graphite fixturing is applied such as to prevent the collared mullite sleeves 2 and tungsten sleeve 3 from sliding down from gravity. Once parts are assembled and fixed, the joint assembly is heated radiantly in vacuum to 1200° C. at 5° C. per minute, at which point 1 atmosphere of argon is vented into the furnace. It is preferable to begin the process in vacuum to assist in removing any excess water vapor, unwanted organics, or any other volatiles that may have been introduced in the preparation process. Once in argon, the joint assembly is further heat to 1540° C. at 5° C. per minute to allow the joining material to achieve a liquid phase, and held at 1540° C. for 3 minutes to allow the joining material to spread evenly within the joint area. The joint is then allowed to cool to room temperature at 5° C. per minute.

Once the Makotite™ joined subassembly is cooled down, it is ready for the final oxidation protective coating of the tungsten 3. To begin, the exposed portions of the sintered tungsten-silicon collars 16 and tungsten are wrapped with a single layer of 0.005 in. thick 80/20 nickel-chromium foil. The entire subassembly with the foil wrapped parts is then placed on a graphite stand and heated radiantly to 1425° C. in argon to allow the foil to melt and coat the tungsten and sintered tungsten-silicon collars 16, and to densify the sintered tungsten-silicon collars 16. Upon cooling, the subassembly can be provided this additional oxidation protection using conventional electroplating techniques by plating alternating layers of nickel to a thickness of 40 microns per layer, followed by chromium to a thickness of 10 microns per layer onto the tungsten sleeve 3 and tungsten-silicon collars 16. These layers are applied until a final plating thickness of 200 microns is achieved. Once complete, this results in an oxidation protective coating for the tungsten 3 good to 1000° C.

With two levels of oxidation protection complete, this subassembly is now ready for joining the tungsten 3 circumference to the Inconel tube 11. For this final joining step, the Inconel-600 tube 11 is first interference fit to the tungsten tube 3 to create a seal. Then, with the assembly standing vertically such that the Inconel tube 11 is at the bottom, a ring of 1 mm diameter copper wire is placed between the superalloy 11 and tungsten tubes 3 in a capture groove 15, such as in FIG. 14. Finally, the nickel-chromium alloy powder is packed on top of the copper wire. This joint is then heated to 800° C. in vacuum, at which point an atmosphere of inert gas such as Argon gas is added and the temperature is raised to 1200° C. for 1-5 minutes. The assembly is then allowed to cool to room temperature to complete the joining process. The joined assembly, as shown in FIG. 14, is now a complete helium gas tight and strong component ready to be used to a service temperature of up to 1000° C.

REFERENCES, all of which are incorporated by reference herein.

[1] T. J. Clark, M. J. Flanagan, R. W. Cruse, K. Park, V. A. Szalai, S. J. Rohman, R. M. Mininni, U.S. Pat. No. 5,208,069 May 4, 1993 and EP0540084 B1 Sep. 4, 1996.
[2] F. M. Mako, R. Silberglitt, L. K. Len, Pulsed Electron Beam Joining of Materials, (Israel) Pat. No. 118126/2 (Oct. 3, 1994).
[3] F. M. Mako, R. Silberglitt, L. K. Len, Pulsed Electron Beam Joining of Materials, U.S. Pat. No. 5,599,468 (Feb. 4, 1997).
[4] F. M. Mako, R. L. Bruce, Ceramic Joining, U.S. Pat. No. 6,692,597 B2 (Feb. 17, 2004).
[5] F. M. Mako, R. L. Bruce, Ceramic Joining, PRC (China) Pat. No. ZL02824111.8 (Jun. 11, 2008).
[6] F. M. Mako, R. L. Bruce, Ceramic Joining, U.S. Pat. No. 8,337,648 B2 (Dec. 25, 2012).

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An assembly comprising:
   a ceramic body;
   a tungsten coupling attached to the ceramic body with a first joint that forms a first helium tight seal between the ceramic body and the tungsten coupling and where the first helium tight seal maintains its integrity at a temperature over 400° C.; and
   a metal body attached to the tungsten coupling with a second joint that forms a second helium tight seal between the metal body and the tungsten coupling and where the second helium tight seal maintains its integrity at a temperature over 400° C., the ceramic body, the tungsten coupling and the metal body are hollow and form a continuous channel extending through and inside the ceramic body, the tungsten coupling, the metal body and the first and second helium tight seals, the ceramic body is made of silicon carbide and the metal body is made of super alloy, the first joint is made of between 30 wt % (weight percent or percent by mass) and 80 wt %, nominally 60 wt %, aluminum-silicate, and between 20 wt % and 70 wt % magnesium-silicate, also known as Steatite.

2. The assembly of claim 1 wherein the second joint is made of a mixture of 10 wt %-80 wt % 80/20 nickel-chromium alloy powder, and 20 wt %-90 wt % copper wire or grain of ≥99.99% purity.

3. The assembly of claim 2 wherein the metal body attached to the tungsten coupling attached to the ceramic body aligned to define a straight line.

4. The assembly of claim 3 wherein the metal body attached to the tungsten coupling attached to the ceramic body defining band.

5. An assembly comprising:
   a ceramic body;
   a tungsten coupling attached to the ceramic body with a first joint that forms a first helium tight seal between the ceramic body and the tungsten coupling and where the first helium tight seal maintains its integrity at a temperature over 400° C.; and
   a metal body attached to the tungsten coupling with a second joint that forms a second helium tight seal between the metal body and the tungsten coupling and where the second helium tight seal maintains its integrity at a temperature over 400° C., the ceramic body, the tungsten coupling and the metal body are hollow and form a continuous channel extending through and inside the ceramic body, the tungsten coupling, the metal body and the first and second helium tight seals, the ceramic body is made of silicon carbide and the metal body is made of super alloy, the first joint is made of between 16.8 wt % and 35.8 wt %, nominally 28.2 wt %, alumina, between 57.9 wt % and 61.2 wt %, nominally 59.2 wt %, silica and between 6.3 wt % and 22.0 wt %, nominally 12.6 wt %, magnesia.

6. An assembly comprising:
   a ceramic body;
   a tungsten coupling attached to the ceramic body with a first joint that forms a first helium tight seal between the ceramic body and the tungsten coupling and where the first helium tight seal maintains its integrity at a temperature over 400° C.; and
   a metal body attached to the tungsten coupling with a second joint that forms a second helium tight seal between the metal body and the tungsten coupling and where the second helium tight seal maintains its integrity at a temperature over 400° C., the coupling has a member which is hollow having an outer surface and an inner surface about the hollow, a coating disposed on the inner and outer surface entirely so no portion of any surface of the member is exposed, the coating made of an oxidation resistant material so the member maintains its integrity above 400 degrees C. and does not oxidize.

* * * * *